United States Patent
Ghansham

(10) Patent No.: US 9,414,962 B2
(45) Date of Patent: Aug. 16, 2016

(54) DEVICE FOR TREATMENT OF GLAUCOMA AND PREVENTION OF SUB-SCLERAL FIBROSIS AND BLOCKAGE

(71) Applicant: Das Agarwal Ghansham, Kolkata (IN)

(72) Inventor: Das Agarwal Ghansham, Kolkata (IN)

( * ) Notice: Subject to any disclaimer, the term of this patent is extended or adjusted under 35 U.S.C. 154(b) by 185 days.

(21) Appl. No.: 14/359,365

(22) PCT Filed: Apr. 22, 2013

(86) PCT No.: PCT/IN2013/000261
§ 371 (c)(1),
(2) Date: May 20, 2014

(87) PCT Pub. No.: WO2013/160910
PCT Pub. Date: Oct. 31, 2013

(65) Prior Publication Data
US 2014/0323945 A1    Oct. 30, 2014

(30) Foreign Application Priority Data

Apr. 23, 2012   (IN) .............................. 453/KOL/2012

(51) Int. Cl.
*A61B 19/00*   (2006.01)
*A61F 9/007*   (2006.01)

(52) U.S. Cl.
CPC .................................. *A61F 9/00781* (2013.01)

(58) Field of Classification Search
CPC .............................. A61F 9/007; A61F 9/00781
USPC ............................................................ 604/8
See application file for complete search history.

(56) References Cited

U.S. PATENT DOCUMENTS

| | | |
|---|---|---|
| 3,993,071 A | 11/1976 | Higuchi et al. |
| 4,521,210 A | 6/1985 | Wong |
| 5,476,445 A * | 12/1995 | Baerveldt ............ A61M 27/002 604/294 |
| 5,882,327 A | 3/1999 | Jacob |
| 6,358,279 B1 | 3/2002 | Tahi et al. |
| 6,464,724 B1 | 10/2002 | Lynch et al. |
| 6,471,666 B1 | 10/2002 | Odrich |
| 6,783,544 B2 | 8/2004 | Lynch et al. |
| 8,348,897 B2 | 1/2013 | Shih et al. |
| 8,353,856 B2 | 1/2013 | Baerveldt |
| 2002/0193725 A1 | 12/2002 | Odrich |
| 2003/0009124 A1 | 1/2003 | Lynch et al. |
| 2003/0055372 A1 | 3/2003 | Lynch et al. |
| 2003/0069637 A1 | 4/2003 | Lynch et al. |
| 2006/0235428 A1 | 10/2006 | Silvestrini |
| 2009/0182310 A1 | 7/2009 | Gertner et al. |
| 2010/0114006 A1 | 5/2010 | Baerveldt |
| 2010/0204786 A1 | 8/2010 | Foulkes |
| 2010/0241046 A1 * | 9/2010 | Pinchuk .................. A61L 27/48 604/8 |
| 2012/0009159 A1 | 1/2012 | Humayun et al. |
| 2013/0102949 A1 | 4/2013 | Baerveldt |
| 2013/0317411 A1 | 11/2013 | Agarwal |

FOREIGN PATENT DOCUMENTS

WO   2008030951 A2   3/2008

* cited by examiner

*Primary Examiner* — Leslie Deak
(74) *Attorney, Agent, or Firm* — The Webb Law Firm

(57) ABSTRACT

A device for treatment of glaucoma and prevention of sub-scleral fibrosis and blockage. This invention relates to a device for treatment of glaucoma comprising of a circular patch (1) with a plurality of holes wherein the patch is made of biocompatible material. Further, this invention also relates to a device for prevention of sub-scleral fibrosis and blockage comprising of a circular patch with a cut integrally provided with a lip (2) wherein the patch is made of bio compatible material and having a plurality of holes.

7 Claims, 2 Drawing Sheets

DEVICE FOR TREATMENT OF GLAUCOMA AND PREVENTION OF SUB-SCLERAL FIBROSIS AND BLOCKAGE

CROSS-REFERENCE TO RELATED APPLICATIONS

This application is the United States national phase of International Application No. PCT/IN2013/000261 filed Apr. 22, 2013, and claims priority to Indian Patent Application No. 453/KOL/2012 filed Apr. 23, 2012, the disclosures of which are hereby incorporated in their entirety by reference.

FIELD OF INVENTION

This invention relates to a device for treatment of glaucoma and prevention of sub-scleral fibrosis and blockage.

BACKGROUND OF INVENTION

Glaucoma is commonly known eye related disease, in which the pressure of anterior chamber of eye increases, which may lead to blindness if left untreated.

A number of treatments for glaucomais known to have been provided. It includes drops and medications for milder forms and surgical treatment in the form of "trabeculectomy" or filtering surgery & glaucoma shunt.

In case of trabeculectomy, an initial pocket is created under conjunctiva & Tenon's capsule. A flap of partial thickness with its base at corneoscleral junction is provided in the sclera. There is also a provision of window opening under the flap with a punch to remove a portion of sclera, Schlemm's canal & trabecular meshwork so as to enter anterior chamber of eye.

The result of this operation is that, scleral flap either does not heal or heals very poorly. Hence, the track thus created allows anterior chamber fluid to come out and get absorbed under the conjunctiva. However, it is associated with a drawback that, due to fibroblast proliferation the conjunctival wound heals, but leads to failure with time.

To overcome the above, antimetabolites such as mitomycin C or 5 fluorouracil is used. The anticancer drugs prevent healing/fibroblast proliferation at the site. The problem due to poor healing complications are more common. However, it is still most commonly adopted procedure.

Alternatively, a collagen sponge is placed on top of scleral flap, which gets absorbed with time. During healing phase the fibroblast network thus formed becomes loose, that allows movement & absorption of fluid.

Therefore, a novel device for treatment of glaucoma is required to be developed to further improve and simplify the procedure.

Hence, the present invention has been proposed for treatment of glaucoma and prevention of sub-scleral fibrosis and blockage.

SUMMARY OF THE INVENTION

The primary object of this invention is to propose a device for treatment of glaucoma which overcomes, disadvantages associated with the prior art.

Another object of this invention is to propose a device for treatment of glaucoma to avoid use of animal protein (collagen) for treatment of Glaucoma.

Another object of this invention is to propose a device for treatment of glaucoma to avoid use of antimetabolite (anticancer drugs) thereby reducing the complication rates.

Further object of this invention is to propose a device for treatment of glaucoma to improve results of filtration operation for glaucoma surgery.

Yet another object of this invention is to a device for treatment of glaucoma which is simple, effective and cost effective.

Yet another object of this invention is to prevent fibrosis of conjunctiva with sclera to maintain a space between sclera & conjunctiva.

Further another object of this invention is to prevent sub-scleral fibrosis (fibrosis under the sclera flap) to maintain passage to allow flow of fluid.

Still another object of this invention is to propose a device for prevention of sub-scleral fibrosis and blockage which is efficient.

Yet another object of this invention is to propose a device for prevention of sub-scleral fibrosis and blockage which is reliable.

According to this invention, there is provided a device for treatment of glaucoma comprising of a circular patch with a plurality of holes wherein the patch is made of biocompatible material.

Further, according to this invention there is provided a device for prevention of sub-scleral fibrosis and blockage comprising of a circular patch with a cut integrally provided with a lip wherein the patch is made of bio compatible material and having a plurality of holes.

BRIEF DESCRIPTION OF THE ACCOMPANYING DRAWINGS

Further objects and advantages of this invention will be more apparent from the ensuing description when read in conjunction with the accompanying drawings and wherein.

DETAILED DESCRIPTION OF THE INVENTION

The present invention is directed to a device for treatment of glaucoma and prevention of sub-scleral fibrosis and blockage. Said device comprising of a patch of inert material. The patch is very thin along with a plurality of holes. Said patch is made of biologically inert material.

The diameter and thickness of patch may vary from 6-16 mm and 0.5 mm to 1.5 mm respectively. The diameter of holes in the patch ranges from 0.1 mm to 2 mm. The material is such as medical grade silicone elastomer, tetrafluoro polyethylene PTFE sheet or fibrous sheet of same material or other biocompatible materials.

Now, reference may be made to FIG. 1 indicating patch (1) of inert material described hereinabove.

The patch is positioned on top of the sclera flap to cover the distal part of sclera flap.

Figures 1, 2:
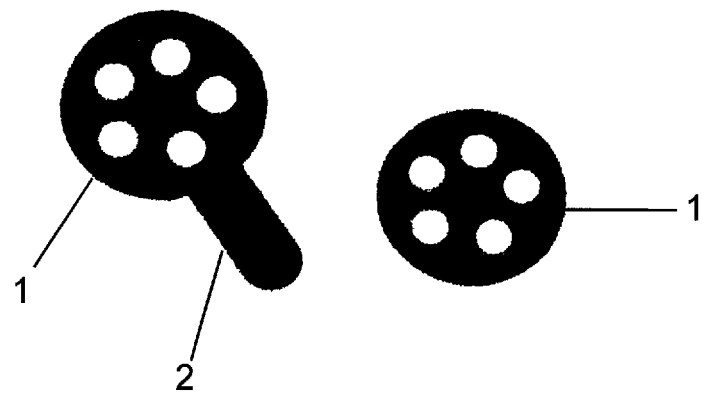
FIG. 1 shows: an exemplary embodiment of the present invention with lip.
FIG. 2 shows: another exemplary embodiment of the present invention without lip.

Further, referring to FIG. 2 showing another embodiment. In this the patch (1) is provided with a projected lip (2).

The lip is inserted under the scleral flap & the main patch is kept under conjunctiva over sclera. This maintains a passage for fluid from anterior chamber to under the conjunctiva. Thus, the filtering bleb and passage are maintained without occurrence of undesirable healing and obliteration of passage and bleb. The length and width of said lip is 3-10 mm and 2-6 mm respectively.

Thus, the instant invention is provided to prevent healing of conjunctiva with sclera. Further, these patches maintain a space/pocket between two structure.

A typical example is 0.7 mm thick patch with 10 mm diameter and a 5 mm long with 3 mm wide lip made of silicone elastomer or PTFE. Also, five holes of 1.5 mm diameter are provided.

Figure 3:
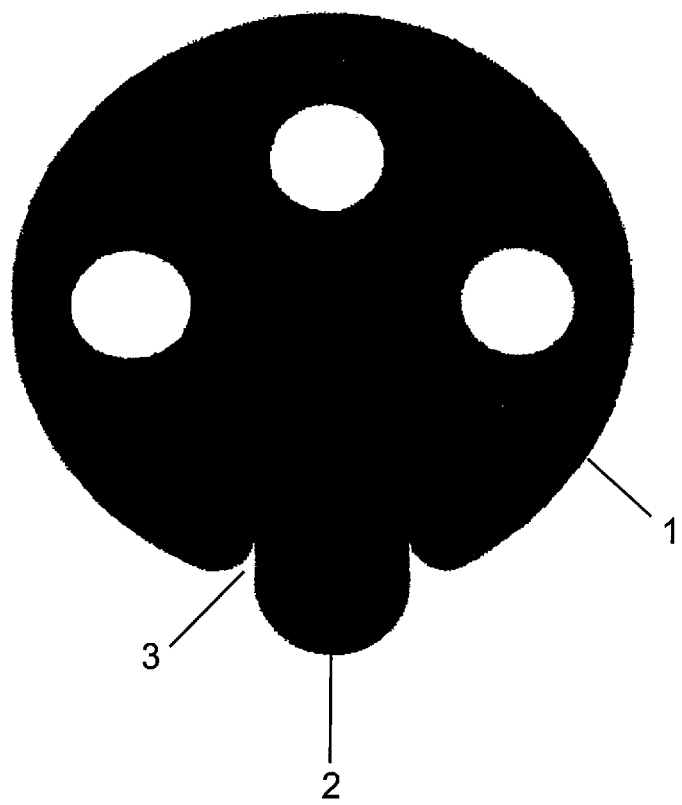
FIG. 3 shows: still another exemplary embodiment of device of the present invention for prevention of sub-scleral fibrosis and blockage.

Now, reference may be made to still another embodiment as shown in FIG. 3, wherein a round patch (1) with a cut (3) is provided. Said round patch comprising of a plurality of holes. Further, a lip (2) is integrally provided with the round patch as shown.

The length and width of said lip is 3-10 mm and 2-6 mm respectively. The diameter of holes in the patch is 0.1-2 mm.

The lip (2) is inserted under sclera and U section (1) remains on the top of sclera. It maintains the passage from anterior chamber to under sclera flap and to under the conjunctiva. This is very useful for failed trabeculectomy. Patient is saved from disfigurement of a second trabeculectomy. Further, it helps in opening up of existing trabeculectomy.

The aforesaid embodiment is provided to prevent healing of conjunctiva with sclera and also for healing of sclera to sclera flap. Further, these patches maintain a space/pocket between two structure.

A typical example is 0.7 mm thick patch with 10 mm diameter and a 5 mm long with 3 mm wide lip made of silicone elastomer or PTFE. Also, three holes of 1.5 mm diameter are provided as shown in FIG. 3.

It is to be noted that the present invention is susceptible to modifications, adaptations and changes by those skilled in the art. Such variant embodiments employing the concepts and features of this invention are intended to be within the scope of the present invention, which is further set forth under the following claims:

I claim:

1. A device for prevention of sub-scleral fibrosis and blockage comprising of a round patch having a lip with a cut integrally provided in the patch adjacent the lip, wherein the patch is made of a biocompatible material and has a plurality of holes;
   wherein the lip has a portion proximal the patch and a portion distal the patch, and wherein the cut integrally provided in the patch is arranged such that the portion of the lip proximal the patch is radially inward of the circumference of the patch material.

2. The device as claimed in claim 1, wherein the biocompatible material is selected from the group consisting of medical grade silicone elastomer, tetrafluoro polyethylene PTFE sheet, and fibrous sheets of same material.

3. The device as claimed in claim 1, wherein the patch has a diameter and thickness of 6-16 mm and 0.5 to 1.5 mm, respectively.

4. The device as claimed in claim 1, wherein the diameter of holes in the patch is 0.1 mm to 2 mm.

5. The device as claimed in claim 1, wherein the length and width of the lip are 3-10 mm and 2-6 mm, respectively.

6. The device as claimed in claim 1, wherein the cut integrally provided in the patch comprises a slit extending radially inward of the circumference of the circular patch.

7. A method of preventing sub-scleral fibrosis and blockage comprising:
   providing a round patch having a lip with a cut integrally provided in the patch adjacent the lip, wherein the patch is made of a biocompatible material and has a plurality of holes;
   wherein the lip has a portion proximal the patch and a portion distal the patch, and wherein the cut integrally provided in the patch is arranged such that the portion of the lip proximal the patch is radially inward of the circumference of the patch material; and
   inserting the patch under a section of sclera of a patient's eye, wherein the lip and cut remain on top of the sclera.

* * * * *